(12) United States Patent  
Ferko

(10) Patent No.: US 7,780,641 B2
(45) Date of Patent: Aug. 24, 2010

(54) TRANSCECAL ILEOSTOMY SET

(75) Inventor: Alexander Ferko, Vysoka nad Labem (CZ)

(73) Assignee: Cedars-Sinai Medical Center, Los Angeles, CA (US)

( * ) Notice: Subject to any disclaimer, the term of this patent is extended or adjusted under 35 U.S.C. 154(b) by 597 days.

(21) Appl. No.: 11/763,309

(22) Filed: Jun. 14, 2007

(65) Prior Publication Data

US 2008/0312614 A1    Dec. 18, 2008

(51) Int. Cl.
*A61F 5/44* (2006.01)

(52) U.S. Cl. .................. 604/332; 604/333; 604/334; 604/335; 604/336; 604/337; 604/338; 604/339; 604/340; 604/341; 604/342; 604/343; 604/344; 604/345

(58) Field of Classification Search .......... 604/332–345
See application file for complete search history.

(56) References Cited

U.S. PATENT DOCUMENTS

| 3,581,732 | A | | 6/1971 | Ruiz |
| 5,273,529 | A | | 12/1993 | Idowu |
| 5,417,657 | A | | 5/1995 | Hauer |
| 5,813,976 | A | | 9/1998 | Filipi et al. |
| 6,461,327 | B1 | | 10/2002 | Addis et al. |
| RE38,711 | E | * | 3/2005 | Igaki et al. ............... 606/198 |
| 2002/0193806 | A1 | * | 12/2002 | Moenning et al. .......... 606/108 |

| 2004/0111061 | A1 | | 6/2004 | Curran |

FOREIGN PATENT DOCUMENTS

| EP | 1 779 823 | | 2/2007 |
| GB | 846 779 | | 8/1960 |
| GB | 846779 | * | 8/1960 |
| WO | 98/15309 A1 | | 4/1998 |
| WO | 00/41759 A1 | | 7/2000 |
| WO | 00/48658 A1 | | 8/2000 |
| WO | 01/49224 | | 7/2001 |
| WO | 02/26293 | | 4/2002 |
| WO | 2006/010556 | | 2/2006 |

OTHER PUBLICATIONS

Motycka, P. et al., "Diverting Ileostomy Set Removable Without Laparotomy—Feasibility Study", European Surgical Research, 2006, 38:365-369.

* cited by examiner

*Primary Examiner*—Tatyana Zalukaeva
*Assistant Examiner*—Ilya Y Treyger
(74) *Attorney, Agent, or Firm*—Seth D. Levy; Davis Wright Tremaine LLP

(57) ABSTRACT

Described herein is a transcecal ileostomy set including a balloon catheter equipped with a blocking balloon, which serves for obstruction of a small intestine, and a fixation balloon, which serves for fixation of the balloon catheter inside the large intestine when inflated. Furthermore, it includes a holder, adapted to be fixed to a patient's body from the outside, which serves for closing a large intestine wall by tightening a bioresorbable loop passing through the large intestine wall and abdominal wall. A rotary part of the plastic holder may be affixed with a protrusion serving as a block when turning to tighten the bioresorbable loop.

4 Claims, 2 Drawing Sheets

TRANSCECAL ILEOSTOMY SET

FIELD OF THE INVENTION

This invention relates generally to medical devices. More particularly, the field of art into which this invention falls is ileostomy sets used for drainage and collection of feces straight from the ileum (i.e., the large intestine is bypassed) through the abdominal wall.

BACKGROUND OF THE INVENTION

The following description includes information that may be useful in understanding the present invention. It is not an admission that any of the information provided herein is prior art or relevant to the presently claimed invention, or that any publication specifically or implicitly referenced is prior art.

An ileostomy is a surgical procedure wherein the small intestine is attached to the abdominal wall. A stoma is created to provide a pathway for digestive waste to exit the body. After the ileostomy, the large intestine is bypassed. An ileostomy is used to treat many conditions, including bowel obstructions, cancer of the colon and/or rectum, colitis, Crohn's disease, congenital bowel defects, and injury to the intestinal tract. An ileostomy may be temporary in nature. A temporary ileostomy is performed in patients undergoing small bowel resection, patients with colorectal cancer, or where an ileoanal pouch anastomosis (IPAA) is created. There remains a need in the art for new devices and techniques for the creation of a temporary ileostomy.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described.

Defunctioning surgical loop ileostomy is a standard technique used for temporary diversion for left-sided colon and rectum resections in high-risk patients. When ileostomy is unnecessary anymore, it is taken down. A patient typically undergoes another surgery—laparotomy, during which a loop ileostomy is closed. Even such an operation is associated with mortality and rather high morbidity.

The present invention is based on a special balloon catheter, which allows total drainage of intestinal fluids/feces from the small intestine such that the colon after a resection is bypassed. A bag for collection of intestinal fluids/feces is connected to the balloon catheter outside of the human body. The transcecal ileostomy set of the present invention has been constructed with an intention to close up the ileostomy without surgery (i.e., to spare a patient one operation). The solution of the present invention allows, upon removal of the balloon catheter, closure of the ileostomy by means of a bioresorbable loop that purses the large intestine wall percutaneously.

In addition, the balloon catheter of the present invention is equipped with one more inflatable balloons. Upon insertion of the balloon catheter into the desired place, the balloon is inflated inside the large intestine, which may prevent the balloon catheter from undesirable movement.

Figure 1:
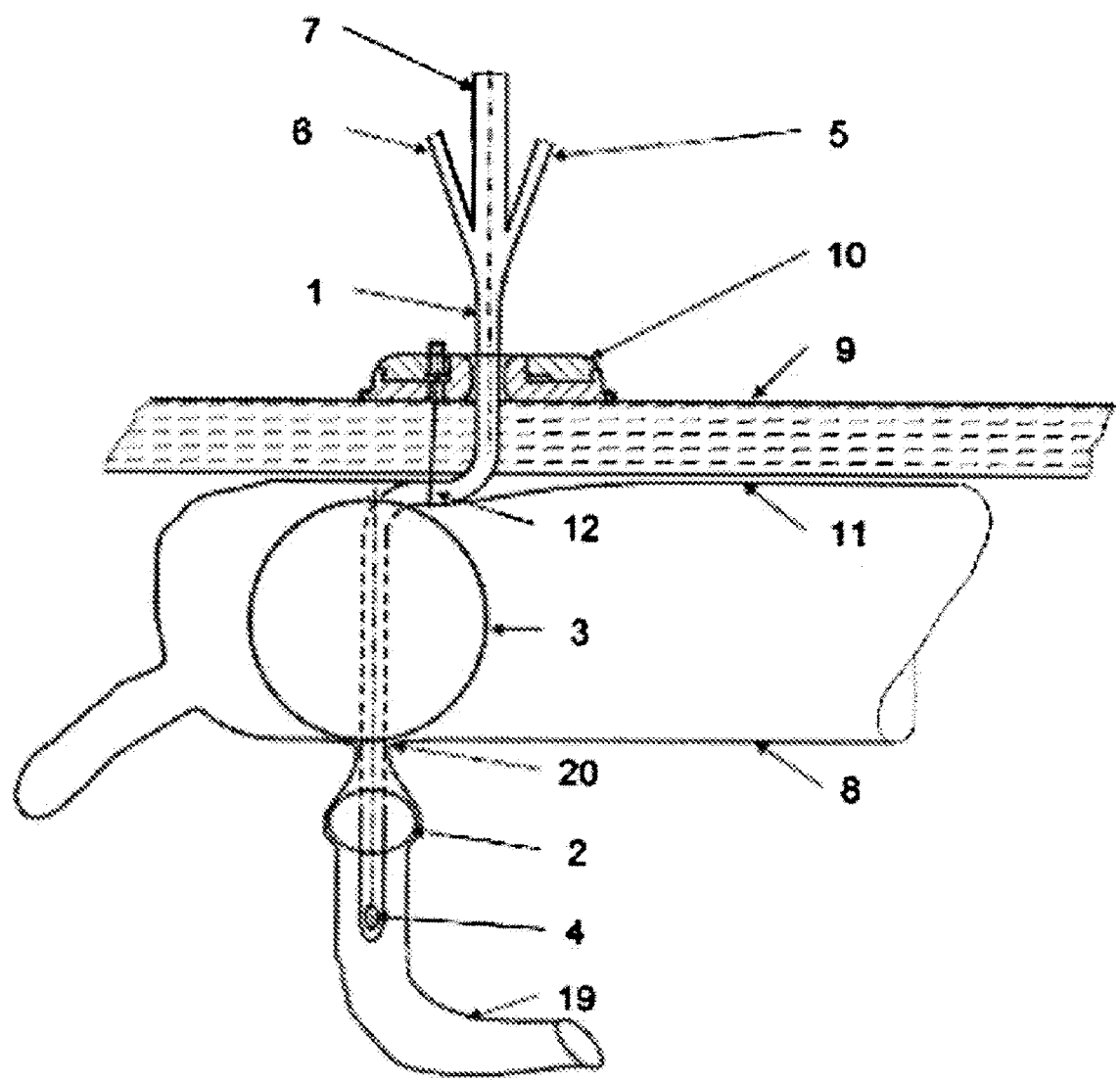
FIG. 1 is a cross-section side view of a transcecal ileostomy set (without the bag for feces) in accordance with an embodiment of the present invention.
Figure 3:
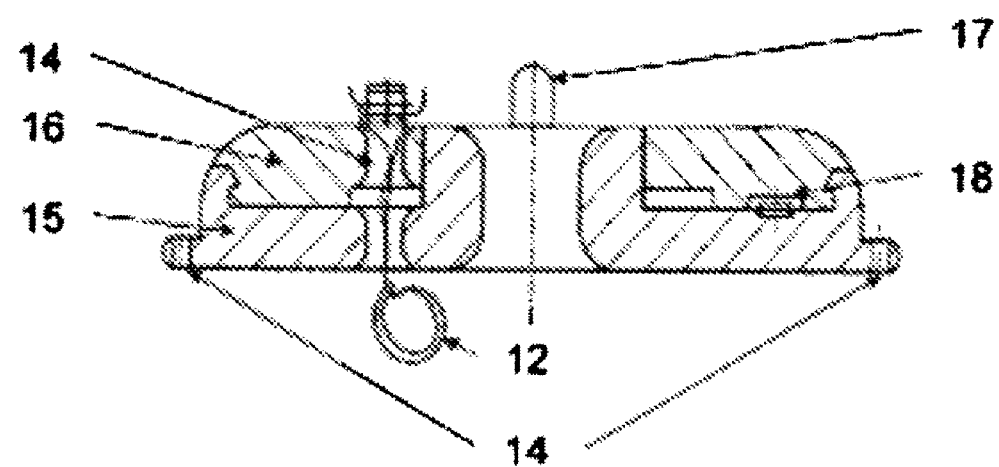
FIG. 3 is a cross-section side view of the plastic holder from FIG. 1 in accordance with an embodiment of the present invention.

FIG. 1 shows a transcecal ileostomy set of the present invention. It includes a balloon catheter 1, equipped with two balloons—blocking balloon 2 and fixation balloon 3—in a distal portion thereof, with a perforation 4 at the distal end. The balloon catheter 1 may be divided into three lumens; one is equipped with a blocking balloon valve 5 at a proximal end, one with fixation balloon valve 6 at a proximal end, and the last one ended with intestinal fluid outlet 7 at its proximal end. The balloon catheter 1 is fastened against movement inside the large intestine 8 by means of the inflated fixation balloon 3 and out of a patient's body on the surface of an abdominal wall 9 by means of a holder 10 that may be constructed from plastic. In addition, the balloon catheter 1 may be fastened to a large intestine wall 11 by using a bioresorbable loop 12. The bioresorbable loop 12 passes through the large intestine wall 11 as well as abdominal wall 9 and is tied or otherwise fixed to the holder 10 (as shown in FIG. 3).

Figure 2:
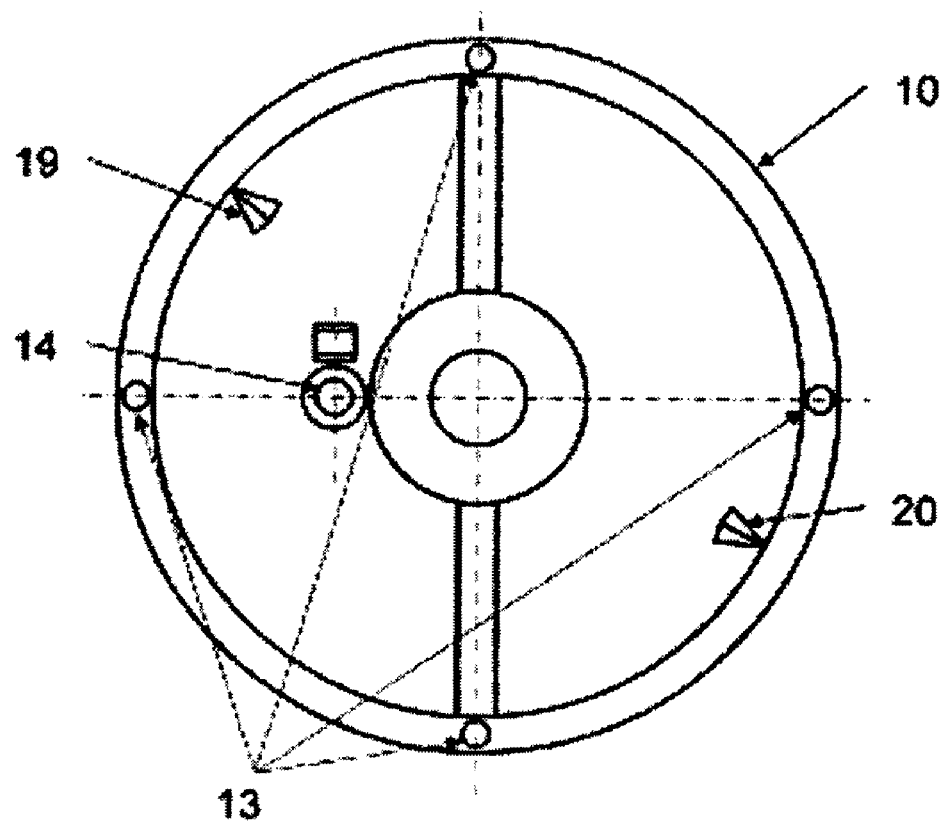
FIG. 2 is a plan view of the plastic holder from FIG. 1 in accordance with an embodiment of the present invention.

The holder 10 is fixed to the outer side of the abdominal wall 9 by using fixing apertures 13 (FIG. 2). Any number and configuration of apertures 13 can be used in accordance with alternate embodiments of the present invention. This serves for holding both balloon catheter 1 and bioresorbable loop 12 in place. The bioresorbable loop 12 passes from the site of incision into the large intestine wall 11 (through which the balloon catheter 1 is inserted) through the abdominal wall 9 and the aperture 14 of both stable 15 and rotary 16 parts of the holder 10 and is tied up thereon (FIG. 3). The rotary part 16 of the holder 10 is affixed with protrusion 17 serving as a block when tightening the bioresorbable loop 12. To tighten the bioresorbable loop 12, the rotary part 16 is turned clockwise; a counterclockwise movement may be blocked by a system of toothing with latch 18. Alternatively, to tighten the bioresorbable loop 12, the rotary part 16 is turned counterclockwise, and a clockwise movement may be blocked by a system of toothing with latch 18.

In one embodiment according to the present invention, the balloon catheter 1 is introduced through a small incision into the large intestine wall 11 such that its distal portion with the fixation balloon 3 is inserted into the large intestine 8 and the blocking balloon 2 into the small intestine 19 behind the Bauhin valve 20 (FIG. 1).

The bioresorbable loop 12 (e.g., monofilamentous surgical suture PDS (absorbable polydioxanone surgical suture)) in this embodiment is placed around the balloon catheter 1 in the shape of purse-string suture to seal space between the balloon catheter 1 and the incision edges on the large intestine wall 11. Other bioresorbable materials suitable for use in connection with alternate embodiments of the present invention will be readily identified by those of skill in the art and can be used in connection with the present invention without undue experimentation. Then, both ends of the bioresorbable loop 12 are threaded through the abdominal wall 9 such to form a lasso-loop (FIG. 3). This lasso-loop holds the large intestine wall 11 to the abdominal wall 9 and allows a closure of the incision after removal of the balloon catheter 1. The proximal end of the balloon catheter 1 is held by the holder 10, which is fixed to the body surface, as shown in FIG. 1.

A syringe may be put on the fixation balloon valve 6 to inflate the fixation balloon 3 to fix the inserted balloon catheter 1 in situ. Then, a syringe may be put on the blocking balloon valve 5 to inflate the blocking balloon 2 to completely obstruct the small intestine 19. The intestinal fluid is thereby forced to flow through the perforation 4 of the balloon catheter 1 and therethrough up to an intestinal fluid outlet 7 at the proximal end of the balloon catheter 1 (that may be connected to, e.g., a common ileostomic bag).

When this device is no longer necessary for a patient and the balloon catheter 1 is to be removed, both blocking balloon 2 and fixation balloon 3 are deflated (e.g., by using a syringe). The balloon catheter 1 may then be removed from a patient's body by simple pulling.

To avoid an intestinal fluid leakage through the incision when the balloon catheter 1 is removed, the large intestine wall 11 may be closed. Turning the rotary part 16 of the holder 10 clockwise from the default position 19 to the position of tightened loop 20 (FIG. 2), the bioresorbable loop 12 purses the large intestine wall 11 until completely closed.

When closed, the large intestine wall 11 may heal in several days; the holder 10 may then be removed. The bioresorbable loop 12 gets resorbed later on, in situ; thus no further intervention is needed.

Various embodiments of the invention are described above in the Detailed Description of the Invention. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

What is claimed is:

1. A transcecal ileostomy set designed for drainage of intestinal fluids from the small intestine, comprising:
   a balloon catheter adapted to be percutaneously introduced through an abdominal wall and a large intestine wall into the small intestine, including
      a fixation balloon affixed to a distal portion of the balloon catheter, and
      a blocking balloon affixed to the distal portion of the balloon catheter; and
   a holder to hold the balloon catheter outside a human body when the transcecal ileostomy set is in use,
   whereby, when the fixation balloon is inflated in the large intestine, it fills substantially an entire lumen thereof, and when the blocking balloon is inflated in the small intestine behind the Bauhin valve, it obstructs substantially an entire lumen thereof, and
   wherein the holder further comprises a stable part adapted to be fixed to a surface of the human body, and a rotary part adapted to tighten a bioresorbable loop by turning, whereby, when the transcecal ileostomy set is in use, the bioresorbable loop purses the large intestine wall until closed.

2. The transcecal ileostomy set of claim 1, wherein the bioresorbable loop comprises absorbable polydioxanone.

3. The transcecal ileostomy set according to claim 1, adapted such that when the rotary part is rotated in a first rotational direction from a default position to a tightened loop position, the bioresorbable loop is simultaneously tightened due to being caught by a protrusion, which simultaneously closes an incision in the large intestine wall.

4. The transcecal ileostomy set according to claim 3, adapted such that rotational movement of the rotary part in a second rotational direction is blocked by a toothing and latch mechanism, wherein the first rotational direction is opposite the second rotational direction.

* * * * *